United States Patent
Knapp et al.

(10) Patent No.: US 7,871,794 B2
(45) Date of Patent: Jan. 18, 2011

(54) ENHANCED CELL-FREE SYNTHESIS OF ACTIVE PROTEINS CONTAINING DISULFIDE BONDS

(75) Inventors: Kurtis G. Knapp, Stanford, CA (US); James Robert Swarts, Menlo Park, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 433 days.

(21) Appl. No.: 12/016,763

(22) Filed: Jan. 18, 2008

(65) Prior Publication Data

US 2008/0248521 A1    Oct. 9, 2008

Related U.S. Application Data

(60) Provisional application No. 60/881,251, filed on Jan. 18, 2007.

(51) Int. Cl.
*C12P 21/40* (2006.01)
*C07K 1/00* (2006.01)

(52) U.S. Cl. .................. 435/68.1; 435/69.1; 435/71.1; 530/402

(58) Field of Classification Search ............... None
See application file for complete search history.

(56) References Cited

U.S. PATENT DOCUMENTS

| | | |
|---|---|---|
| 6,548,276 B2 | 4/2003 | Swartz et al. |
| 7,041,479 B2 | 5/2006 | Swartz et al. |
| 2004/0038332 A1 | 2/2004 | Swartz et al. |

OTHER PUBLICATIONS

Bessette et al., "Efficient folding of proteins with multiple disulfide bonds in the *Escherichia coli* cytoplasm," Proc. Natl. Acad. Sci. USA, 1999, 96(24):13703-13708.

Bukau et al., "The Hsp70 and Hsp60 chaperone machines," Cell, 1998, 92(3):351-366.
Calhoun et al., "Energizing cell-free protein synthesis with glucose metabolism," Biotechnol. Bioeng., 2005, 90 (5):606-613.
Kim et al., "Efficient production of a bioactive, multiple disulfide-bonded protein using modified extracts of *Escherichia coli*," Biotechnol. Bioeng., 2004, 85(2):122-129.
Kim et al., "A highly efficient cell-free protein synthesis system from *Escherichia coli*," Eur. J. Biochem., 1996, 239 (3):881-886.
Kim et al., "Prolonging Cell-Free Protein Synthesis by Selective Reagent Additions," Biotechnol. Prog., 2000, 16 (3):385-90.
Kim et al., "Prolonging Cell-Free Protein Synthesis with a Novel ATP Regeneration System," Biotechnol. Bioeng., 1999, 66(3):180-188.
Missiakas et al., "Protein Folding in the Bacterial Periplasm, Minireview," J Bacteriol., 1997, 179(8):2465-2471.
Noren et al., "A General Method for Site-Specific Incorporation of Unnatural Amino Acids into Proteins," Science, 1989, 244(4901):182-188.
Qiu et al., "Expression of Active Human Tissue-Type Plasminogen Activator in *Escherichia coli*," Appl. Environ. Microbiol., 1998, 64(12):4891-4896.
Richardson et al., "The ins and outs of a molecular chaperone machine," Trends Biochem. Sci., 1998, 23(4):138-143.
Ryabova, "Functional antibody production using cell-free translation: Effects of protein disulfide isomerase and chaperones," Nature Biotechnol., 1997, 15(1):79-84.
Voloshin et al., "Efficient and scalable method for scaling up cell free protein synthesis in batch mode," Biotechnol. Bioeng., 2005, 91(4):516-521.

*Primary Examiner*—Manjunath N Rao
*Assistant Examiner*—Kagnew H Gebreyesus
(74) *Attorney, Agent, or Firm*—Bozicevic, Field & Francis LLP; Pamela J. Sherwood

(57) ABSTRACT

Compositions and methods are provided for the enhanced in vitro synthesis of active polypeptides containing disulfide bonds. In certain embodiments of the invention, the reaction mix includes a biological extract derived from a bacterial cell in which the glutathione reductase gene has been inactivated, which is pre-treated with a low concentration of a sulfhydryl inactivating agent.

21 Claims, 5 Drawing Sheets

Rate of Reduction
- Very Reducing
- Less Reducing
- Stabilized (A)

| Extract | pH | 1 | 10 | 50 | 100 | 600 | 1000 |
|---|---|---|---|---|---|---|---|
| KC6 | 6.6 | 111 | 107 | 97 | 102 | 11 | 0 |
| KGK10 | 6.6 | 24 | 20 | 2 | -4 | | |
| KGK10 - TrxB | 6.6 | 20 | 15 | 1 | -1 | | |

μM IAM (B)

| Extract | pH | 1 | 10 | 50 | 100 | 600 |
|---|---|---|---|---|---|---|
| KGK10 | 5.0 | 23 | 25 | 19 | 22 | |
| KGK10 | 5.3 | 20 | 23 | 16 | 17 | |
| KGK10 | 5.5 | | 22 | 21 | 16 | 0 |
| KGK10 | 5.8 | 23 | 22 | 15 | 11 | -1 |
| KGK10 | 6.0 | 26 | 26 | 13 | 4 | |
| KGK10 | 6.3 | | 21 | 6 | 0 | |
| KGK10 | 6.6 | 24 | 20 | 2 | -4 | |
| KGK10 | 7.0 | 27 | 20 | 2 | -4 | |
| KGK10 | 7.5 | 24 | 20 | 1 | -3 | |
| KGK10 | 8.2 | 28 | 22 | 1 | -3 | |
| KGK10 | 8.4 | 29 | 21 | 0 | -5 | |
| KGK10 | 9.0 | | 24 | 11 | 5 | -7 |
| KGK10 | 9.7 | 25 | 25 | 15 | 10 | |

μM IAM

B

ENHANCED CELL-FREE SYNTHESIS OF ACTIVE PROTEINS CONTAINING DISULFIDE BONDS

FEDERALLY-SPONSORED RESEARCH OR DEVELOPMENT

This invention was made with Government support under contract 0522337 awarded by the National Science Foundation. The Government has certain rights in this invention.

BACKGROUND OF THE INVENTION

*Escherichia coli* is a widely used organism for the expression of heterologous proteins. It easily grows to a high cell density on inexpensive substrates to provide excellent volumetric and economic productivities. Well established genetic techniques and various expression vectors further justify the use of *Escherichia coli* as a production host. However, a high rate of protein synthesis is necessary, but by no means sufficient, for the efficient production of active biomolecules. In order to be biologically active, the polypeptide chain has to fold into the correct native three-dimensional structure, including the appropriate formation of disulfide bonds.

In many cases, the recombinant polypeptides have been found to be sequestered within large refractile aggregates known as inclusion bodies. Active proteins can be recovered from inclusion bodies through a cycle of denaturant-induced solubilization of the aggregates followed by removal of the denaturant under conditions that favor refolding. But although the formation of inclusion bodies can sometimes ease the purification of expressed proteins; in most occasions, refolding of the aggregated proteins remains a challenge.

Various attempts have been made to improve the folding of heterologous proteins in the bacterial cytoplasm. In addition to the traditional methods, including lowering the temperature of the culture, increasing knowledge of the mechanism and effectors of protein folding has enabled new approaches to solve the problem of aggregation.

Studies in vitro have demonstrated that, for the vast majority of polypeptides, folding is a spontaneous process directed by the amino acid sequence and the solvent conditions. Yet, even though the native state is thermodynamically favored, the time-scale for folding can vary from milliseconds to days. Kinetic barriers are introduced, for example, by the need for alignment of subunits and sub-domains. And particularly with eukaryotic proteins, covalent reactions must take place for the correctly folded protein to form. The latter types of reaction include disulfide bond formation, cis/trans isomerization of the polypeptide chain around proline peptide bonds, preprotein processing and the ligation of prosthetic groups. These kinetic limitations result in the accumulation of partially folded intermediates that contain exposed hydrophobic 'sticky' surfaces which promote self-association and formation of aggregates.

Expression of mammalian proteins is more complicated than bacterial proteins because many of them require intramolecular disulfide bonds for their activity. Thus additional effectors such as foldases and proper redox potential are required to achieve their native structures. Even though the periplasmic space of *Escherichia coli* provides an oxidizing environment as well as folding proteins such as DsbA, B, C, and D, in many cases, simple secretion of complex proteins into the periplasmic space is not sufficient to form correct disulfide bonds.

Accessory proteins known as foldases and chaperones have been found to assist in the proper folding of proteins in vivo. Foldases have a catalytic activity that serves to accelerate rate-limiting covalent steps in folding. Chaperones, on the other hand, perform many functions, the most important of which is to provide an environment for nascent proteins to fold without the competing process of self-association. In addition to the well-characterized molecular chaperones, such as GroEL and DnaK proteins, a number of additional cytoplasmic proteins have been identified to affect the folding of heterologous proteins.

Following the discovery of numerous bacterial or eukaryotic foldases and their specific roles in the oxidation and isomerization of disulfide bonds, many attempts have been made to use those proteins in the periplasmic space or even in the cytoplasm of *Escherichia coli* (see, for example, Bessette et al. (1999)). The co-expression of molecular chaperones has been shown to partially solve the problem of inclusion body formation in the expression of certain recombinant proteins (see, for example, Richardson et al. (1998) *Trends Biochem. Sci.* 23:138-143; and Bukau et al. (1998) *Cell* 92:351-366).

However, the effect of molecular chaperones can be product-specific and the co-expression of each molecular chaperone with the target proteins is often cumbersome. Moreover, in some cases, the expression of a molecular chaperone is detrimental to cell growth. Despite the recent advances, the expression of properly folded mammalian proteins in *Escherichia coli* still remains as a great challenge. This is mainly due to the difficulties in the control of the key parameters for disulfide bond formation including the sulfhydryl redox potential inside the cells.

For several decades, in vitro protein synthesis, also called cell-free protein synthesis (CFPS), has served as an effective tool for lab-scale expression of cloned or synthesized genetic materials. In recent years, in vitro protein synthesis has been considered as an alternative to conventional recombinant DNA technology, because of disadvantages associated with cellular expression. In vivo, proteins can be degraded or modified by several enzymes synthesized with the growth of the cell, and, after synthesis, may be modified by post-translational processing, such as glycosylation, deamidation or oxidation. In addition, many products inhibit metabolic processes and their synthesis must compete with other cellular processes required to reproduce the cell and to protect its genetic information.

Cell-free protein synthesis has the potential to replace bacterial fermentation as the technology of choice for the production of many recombinant proteins. The most significant advantage is that all of the resources in the reaction theoretically can be directed toward production of the desired product and not to secondary reactions, e.g., those that maintain the viability of the host cell. In addition, removing the need to maintain host cell viability allows the production of proteins that are toxic to the host cell. Furthermore, the lack of a cellular membrane allows direct access to the reaction volume, allowing for addition of reagents that increase the efficacy of the in vitro synthesis reaction (e.g., increase protein yield).

To compete with standard fermentation processes, it is desirable that in vitro synthesis reactions produce equivalent quantities of biologically active proteins at the same (or better) cost (see Voloshin and Swartz (2005) Biotechnol Bioeng 91:516-21). One element of achieving a cell-free synthesis system that competes with fermentation processes is to employ a low cost energy supply for the reaction. To this end, it was found that glucose, the preferred low-cost substrate for bacterial fermentation, could be used in in vitro synthesis if the pH of the system was stabilized (Calhoun and Swartz (2005) Biotechnol Bioeng 90:606-13).

Many industrially relevant proteins, including mammalian proteins, require disulfide bonds for activity. To promote disulfide bond formation, a buffer of reduced (GSH) and oxidized (GSSG) glutathione can be added to an in vitro synthesis reaction to create an oxidizing environment in which disulfide bonds will form. Unfortunately, GSSG is rapidly reduced during in vitro synthesis reactions by two enzymatic pathways mediated by glutathione reductase (Gor) and thioredoxin reductase (TrxB). Deletion of either glutathione reductase or thioredoxin reductase from the strain used to make the extract had little effect on the rate of reduction of GSSG (Kim and Swartz (2004) Biotechnol Bioeng 85:122-9). Deletion of both gor and trxB results in the mutational conversion of the enzyme AhpC from a peroxiredoxin to a disulfide reductase, a mutation which promotes more rapid growth but also stimulates disulfide bond reduction.

To overcome the shortcomings of the gene-deletion systems, iodoacetamide (IAM) has been added to the extract to derivatize the active site cysteines of TrxB and Gor, thereby inactivating those enzymes (Kim and Swartz (2004) Biotechnol Bioeng 85:122-9; U.S. Pat. No. 6,548,276 and U.S. Pat. No. 7,041,479). While IAM-mediated inactivation of TrxB and Gor is useful for promoting disulfide bond formation, conventional IAM treatment can also result in a reduction in protein yields (Kim and Swartz (2004) Biotechnol Bioeng 85:122-9).

Improvements in in vitro synthesis systems that produce active disulfide bond-containing proteins are of continued interest and are the subject of the present invention.

SUMMARY OF THE INVENTION

Compositions and methods are provided for cell-free synthesis of disulfide bond-containing proteins, wherein the redox conditions in the reaction mix are optimized. Such optimization is achieved, at least in part, by utilization of a reaction mixture comprising a cellular extract derived from a bacterial strain in which the glutathione reductase gene has been genetically modified to be inactive, and the cell extract is treated with low levels of a compound that inactivates free sulfhydryl groups, including, without limitation, iodoacetamide (IAM).

In other embodiments of the invention, the bacterial strain from which the cellular extract is derived is genetically modified such that the thioredoxin reductase coding sequence comprises an affinity tag. In such embodiments, prior to use in the synthetic reactions of the invention, a cellular extract from this bacterial strain is contacted to an affinity resin which selectively binds to the affinity tag and removes the thioredoxin reductase protein from the extract.

In some embodiments, cell-free protein synthesis is performed in a reaction mix comprising an extract from a bacterial strain in which both the thioredoxin reductase and glutathione reductase coding sequences have been genetically altered, as described above.

The treatment of cell extracts with a low concentration of inactivating agent further allows the use of an energy source lacking high energy phosphate bonds, because enzymes necessary for the utilization of such energy sources retain activity in the extract. Examples of such energy sources include glucose and glycolytic intermediates. Such energy sources are desirable because of their low cost as compared to energy sources with high-energy-phosphate bonds, such as phosphoenol pyruvate.

In certain embodiments, a redox buffer is included in the reaction mix to maintain the appropriate oxidizing environment for the formation of proper disulfide bonds, for example by the inclusion of glutathione in an appropriate ratio of oxidized to reduced forms.

In addition to stabilizing the redox potential of the reaction mix, the in vitro synthesis may be further enhanced by the inclusion of accessory proteins that assist in the proper folding of proteins in vivo. Of particular interest is the inclusion of foldases, proteins with a catalytic activity that serve to accelerate rate-limiting covalent steps in folding, e.g. PDI, dsbC, Skp, etc. Other modifications of interest include performing the reactions in the substantial absence of polyethylene glycol, which may be replaced with, e.g. spermidine, spermine, putrescine, and the like. The temperature at which the reaction takes place may be optimized for the protein, e.g. by reducing the temperature to about 25°, about 30°, about 32°, about 35°, about 37°, and the like.

In one embodiment of the invention, methods are provided for screening in vitro synthesis reaction conditions in order to optimize folding and correct formation of disulfide bonds. A plurality of reactions having a stable redox potential are assayed for synthesis of the active form of a protein containing at least one disulfide bond, i.e. a protein that is correctly folded. The reaction conditions are optimized, for example, by inclusion of foldase protein(s), and for temperature. Reactions conditions may also be optimized by varying the level of compounds that irreversibly inactivate free sulfhydryl groups, and the ratio of oxidized to reduced forms of the redox buffer.

DETAILED DESCRIPTION OF THE EMBODIMENTS

Compositions and methods are provided for the cell-free synthesis of biologically active proteins, particularly proteins comprising one or more disulfide bonds. In one embodiment of the invention, prior to initiation of cell-free protein synthesis the reaction mixture is stabilized by inactivation of enzyme(s) involved in endogenous oxidoreductase reactions. In certain of these embodiments, the cell-free synthesis system contains a cellular extract derived from a bacterial strain in which the glutathione reductase gene has been inactivated, and/or in which the thioredoxin reductase gene has been modified to include an affinity tag useful for removal of the protein. Such an extract is treated with low concentrations of a compound that inactivates free sulfhydryl groups, e.g. that irreversibly inactivates free sulfhydryl groups.

These methods are applicable to continuous, semi-continuous and batch reactions. In the semi-continuous system, even where the endogenous reducing enzymes are not inactivated, the level of oxidation of the redox buffer will recover substantially after an extended incubation. The recovery of an oxidizing environment in the reaction chamber allows the synthesized protein to acquire disulfide bonds and activity. However, the extracts with inactivated oxidoreductases provide more rapid formation of bioactive proteins.

For some synthetic reactions, e.g. multiplexed reactions, it is preferable to use batch rather than a semi-continuous system. For batch synthesis methods, the reaction mix is preferably modified to decrease the activity of endogenous enzymes that have reducing activity.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Figure 3:
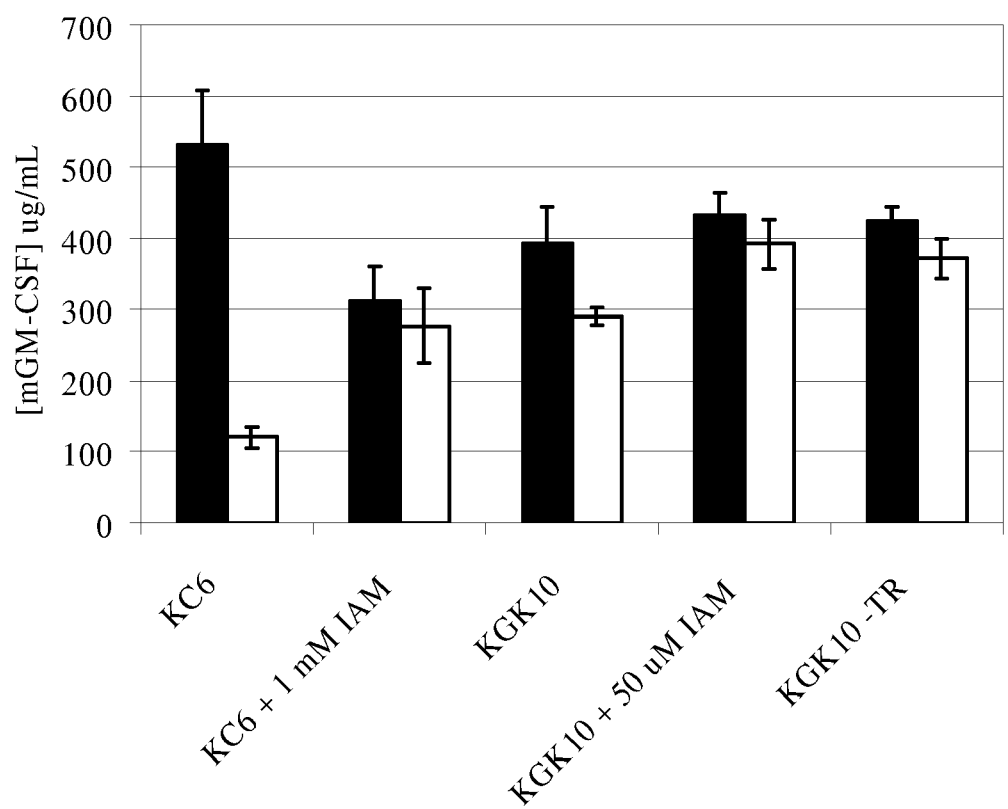
FIG. 3 is a bar graph depicting the in vitro synthesis of mGM-CSF in PANOx-SP reactions with 4 mM GSSG, 1 mM GSH, 100 $\mu$g/mL DsbC, and with the extract pretreated with the indicated concentration of IAM at pH 6.6. The total (black bars) and active (white bars) yields are presented with error bars of +/−one standard deviation for three independent reactions
Figure 4:
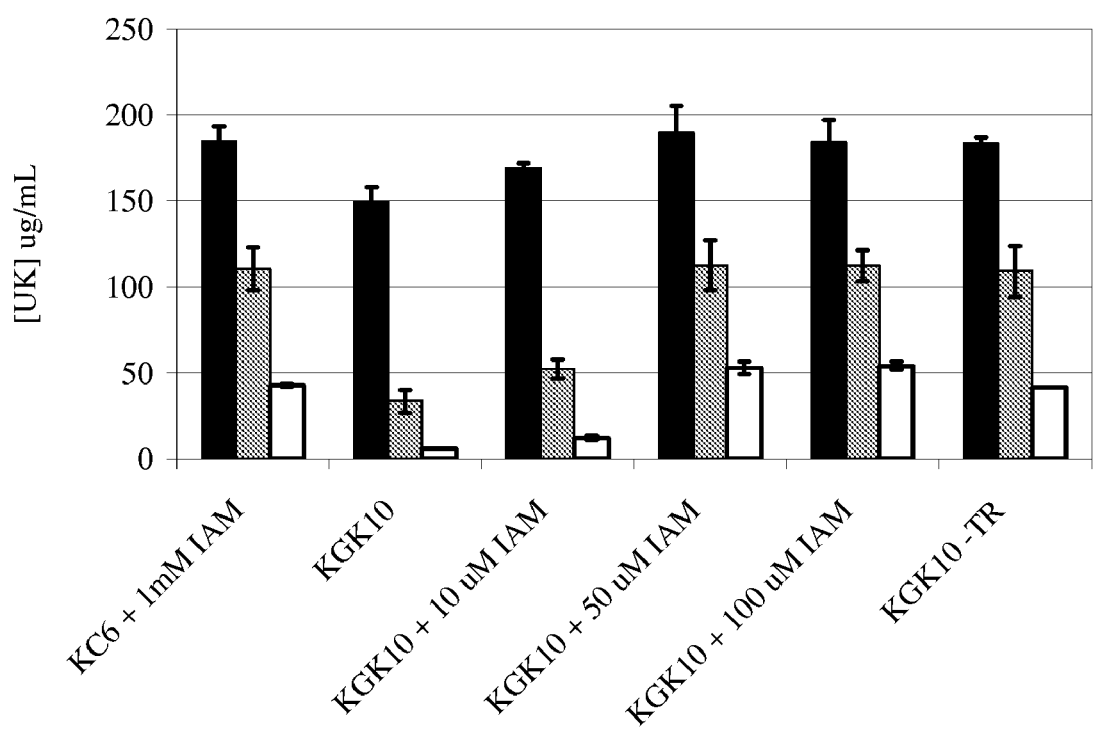
FIG. 4 is a bar graph depicting the in vitro synthesis of urokinase in PANOx-SP reactions with 4 mM GSSG, 1 mM GSH, 75 $\mu$g/mL DsbC, and with the extract pretreated with the indicated concentration of IAM at pH 6.6. The total (black bars), soluble (gray bars), and active (white bars) yields are presented with error bars of +/−one standard deviation for three independent reactions.
Figure 5:
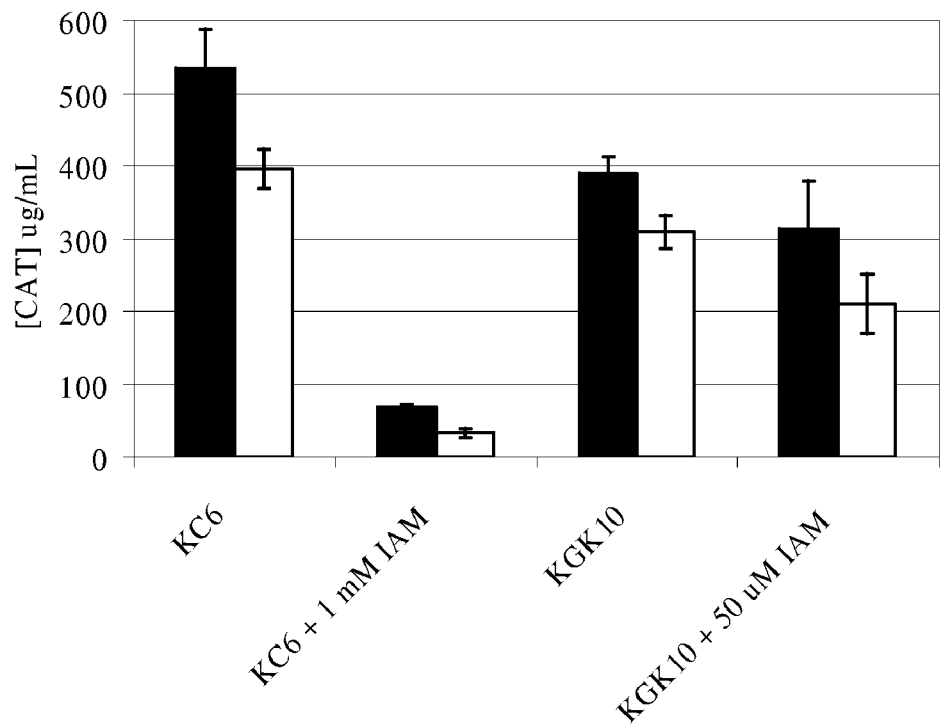
FIGS. 5A and 5B are bar graphs depicting the cell-free production of bacterial and mammalian secreted proteins in reactions fueled with glucose. KC6 and KGK10 extracts were pretreated with the indicated concentration of IAM. (A) in vitro synthesis yields of CAT (B) in vitro synthesis yields of mGM-CSF. The total (black bars) and active (white bars) yields are indicated. The data are an average of six independent reactions, with error bars of +/−one standard deviation.
Figure 5:
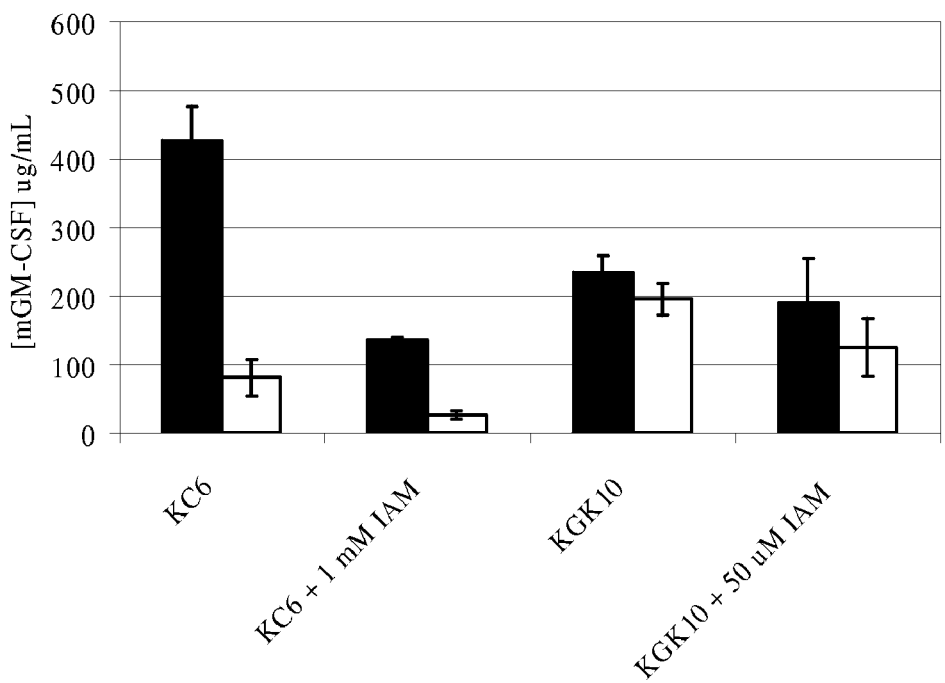

Inactivation of sulfhydryl groups. In the methods of the invention, prior to cell-free synthesis reactions, the cell extract component of a synthetic reaction mix is treated with low concentrations of a compound that chemically blocks sulfhydryl groups, e.g. by alkylation or acetylation of free sulfhydryls. This "low concentration" is a concentration that provides for an increase in the number of properly folded polypeptides in a synthetic reaction, e.g. an increase of at least about 25%, at least about 50%, at least about 100%, at least about 150%, at least about 200% or more as compared to an untreated extract, for example as shown in FIGS. 3-4, while maintaining the ability of the extract in a reaction mix to translate polypeptides and/or transcribe polynucleotides using as an energy source glucose or a glycolytic intermediate lacking high energy phosphate bonds, for example as shown in FIG. 5.

An exemplary "low concentration" of inactivating agent is iodoacetamide at a concentration of at least about 10 µM, about 25 µM, about 50 µM, and not more than about 100 µM. In determining a suitable "low concentration" of inactivating agents other than iodoacetamide, the concentration will provide for a level of inactivation that is equivalent to iodoacetamide at a concentration of at least about 10 µM, about 25 µM, about 50 µM, and not more than about 100 µM. The activity of iodoacetamide may be calculated using the cell-free synthetic methods described herein; or using any convenient assay for iodoacetamide activity, for example as described in any one of Masatomi (1973) J. Biochem. 73:705-716; Vuong et al. (2000) Electrophoresis 21(13):2594-605; Sechi and Chait (1998) Anal Chem. 70(24):5150-8; or Takahashi (1970) J Biochem. 68(4):517-27.

Useful inactivating agents include iodoacetamide, N-ethyl maleimide, iodoacetate, bromoacetate, N-iodoacetyl-N'-(5-sulfonic-1-naphthyl) ethylene diamine, 4-vinylpyridine, acrylamide, etc., as known in the art; especially those compounds including iodoacetamides, maleimides, benzylic halides and bromomethylketones. The concentration of inactivation agent and length of time for the reaction will be determined by the specific compound that is chosen.

The inactivation agent is added at a concentration that substantially eliminates the endogenous sulfhydryl reducing activity in an extract, while maintaining the synthetic activity of the extract. Both activities are readily determined by methods illustrated in the examples provided herein. Usually at least about 50% of the synthetic activity will be retained, more usually at least about 75%, and preferably at least about 90%. As an example, where the inactivation agent is iodoacetamide, it may be added at a concentration of from about 10 to about 50 µM, and incubated from between 15 to 60 minutes.

Folding, as used herein, refers to the three-dimensional structure of polypeptides and proteins or the process of attaining such a structure, where interactions between amino acid residues act to stabilize the structure. While non-covalent interactions are important in determining structure, usually the peptides and proteins of interest will have intra- and/or intermolecular covalent bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

In vitro synthesis: as used herein refers to the cell-free synthesis of macromolecules, usually protein translation, in a reaction mix comprising biological extracts and/or defined reagents. The reaction mix will comprise an energy source; a template for production of the macromolecule, e.g. DNA, mRNA, etc.; amino acids, and such co factors, enzymes and other reagents that are necessary for the synthesis, e.g. ribosomes, tRNA, polymerases, transcriptional factors, etc.

The reaction mixture will also include nucleotides to serve as energy carriers and as building blocks for nucleic acids. Although the triphosphate forms are required, the nucleotides can be added with any number of phosphate groups attached as long as the reaction mixture is activated to convert those forms into the triphosphate forms. These reagents are typically added from at least about 0.1 mM, at least about 0.25 mM, at least about 0.5 mM, and not more than about 2 mM concentrations. Such concentrations that are not sufficient to supply energy for significant protein production without repeated regeneration to the triphosphate form.

In one example of a reaction mixture, glucose is added at about 20 to about 50 mM concentrations to be processed through central catabolism thereby regenerating the ATP, GTP, CTP, and UTP required for transcription and translation. In other examples, glucose or glycolytic or TCA cycle intermediates are slowly fed to a batch system, or the system operated as a continuous system using methods known in the art with, for example, from about 10 mM to about 50 mM glucose in the feed solution.

Such synthetic reaction systems are well-known in the art, and have been described in the literature. The cell-free synthesis reaction may be performed as batch, continuous flow, or semi-continuous flow, as known in the art.

In some embodiments, the synthetic reactions are performed in the substantial absence of polyethylene glycol (PEG), e.g. PEG at a concentration of less than about 0.1%, and may be less than about 0.01%. A conventional reaction mixture contains about 2% poly(ethylene glycol) 8000. However it is found that this diminishes the yield. In the present methods, the molecules spermidine and putrescine can be used in the place of PEG. Spermine or spermidine is then present at a concentration of at least about 0.5 mM, usually at least about 1 mM, preferably about 1.5 mM, and not more than about 5 mM. Putrescine is present at a concentration of at least about 0.5 mM, preferably at least about 1 mM, preferably about 1.5 mM, and not more than about 5 mM.

Glucose or glycolytic intermediate energy source, as used herein, refers to compounds that provide energy for the synthesis of ATP from ADP, and which are part of the glycolytic pathway. These energy sources include glucose, glucose-1-phosphate, glucose-6-phosphate, fructose-6-phosphate, fructose-1,6-diphosphate, triose phosphate, 3-phosphoglycerate, 2-phosphoglycerate, phosphoenol pyruvate (PEP) and pyruvate.

The energy source may be supplied as a suitable biologically acceptable salt or as the free acid, e.g. pyruvic acid, where applicable. The final concentration of energy source at initiation of synthesis will usually be at least about 5 mM, more usually at least about 10 mM, at least about 20 mM, and not more than about 1000 mM, usually not more than about 100 mM. Additional amounts may be added to the reaction mix during the course of synthesis to provide for longer reaction times.

In some embodiments the reaction mixture will comprise nucleotide triphosphates at a concentration of less than about 2.5 mM, and an energy source lacking high energy phosphate bonds, usually glucose or a glycolytic intermediate lacking high energy phosphate bonds, e.g. glucose-6-phosphate, glyceraldehyde-3-phosphate, fructose-6-phosphate, pyruvate, etc. at a concentration of at least about 10 mM. The reactions may be performed in the absence of an exogenous source of high energy phosphate bonds other than the nucleotide triphosphates as set forth above.

Biological extracts. For the purposes of this invention, biological extracts are any preparation comprising the components of protein synthesis machinery, usually a bacterial cell extract, wherein such components are capable of translating a nucleic acid encoding a desired protein. Thus, a bacterial extract comprises components that are capable of translating messenger ribonucleic acid (mRNA) encoding a desired protein, and optionally comprises components that are capable of transcribing DNA encoding a desired protein. Such components include, for example, DNA-directed RNA polymerase (RNA polymerase), any transcription activators that are required for initiation of transcription of DNA encoding the desired protein, transfer ribonucleic acids (tRNAs), aminoacyl-tRNA synthetases, 70S ribosomes, N10-formyltetrahydrofolate, formylmethionine-tRNAfMet synthetase, peptidyl transferase, initiation factors such as IF-1, IF-2 and IF-3, elongation factors such as EF-Tu, EF-Ts, and EF-G, release factors such as RF-1, RF-2, and RF-3, and the like.

For convenience, the organism used as a source of extracts may be referred to as the source organism. In certain embodiments of the invention, the reaction mixture comprises extracts from bacterial cells, e.g. $E.\ coli$ S30 extracts, as is known in the art. May different types of bacterial cells have been used for these purposes, e.g. $Pseudomonas$ sp., $Staphylococcus$ sp., $Methanococcus$ sp., $Methanobacterium$ sp., $Methanosarcina$ sp., etc. In certain of these embodiments, the bacterial cell contains a deletion or directed mutation of a specific gene. Specific genetic modifications of interest include modifications to thioredoxin reductase and/or glutathione reductase. For example, glutathione reductase may be inactivated by deletion, insertion of stop codons, etc. Thioredoxin reductase may be altered by addition of an affinity tag, e.g. his tag, HA tag, etc.

In one embodiment of the invention, the reaction mixture comprises extracts from bacterial cells, e.g. $E.\ coli$ S30 extracts, as is known in the art. Methods for producing active extracts are known in the art, for example they may be found in Pratt (1984), Coupled transcription-translation in prokaryotic cell-free systems, p. 179-209, in Hames, B. D. and Higgins, S. J. (ed.), Transcription and Translation: A Practical Approach, IRL Press, New York. Kudlicki et al. (1992) $Anal\ Biochem$ 206(2):389-93 modify the S30 $E.\ coli$ cell-free extract by collecting the ribosome fraction from the S30 by ultracentrifugation. While such extracts are a useful source of ribosomes and other factors necessary for protein synthesis, they can also contain small amounts of enzymes responsible for undesirable side-reactions that are unrelated to protein synthesis, but which modulate the oxidizing environment of the reaction, and which can act to reduce the groups on the nascent polypeptide and the redox buffer.

The thioreductase genes may be described with reference to the $E.\ coli$ sequences, e.g. as set forth in the reference K12 strain genome, Genbank accession number NC_000913, version NC_000913.2 GI:49175990. The glutathione reductase gene (gor) is positioned as residues 3644322-3645674 of the genome. The enzyme has the EC classification 1.8.1.7. The $E.\ coli$ protein may be referenced at Genbank, NP_417957.1.

The thioredoxin reductase gene (trxB) is positioned as residues 930308-931273 (complement) of the $E.\ coli$ genome. The enzyme has the EC classification 1.8.1.9. The $E.\ coli$ protein may be referenced at Genbank, NP_415408.1.

The coding sequence for an enzyme may be "knocked-out" or otherwise inactivated in the chromosome of the source organism, by deletion of all or a part of the coding sequence; frame-shift insertion; dominant negative mutations, etc. The genomes of a number of organisms, including $E.\ coli$, have been completely sequenced, thereby facilitating the genetic modifications. For example, a markerless knockout strategy method is described by Arigoni et al. (1998) Nat Biotechnol 16(9):851-6.

A method for inactivating targeted genes is described by Hoang et al. (1998) Gene 212:77-86. In this method, gene replacement vectors are employed that contain a tetracycline resistance gene and a gene encoding levan sucrase (sacB) as selection markers for recombination. The target gene is first cloned and mutagenized, preferably by deleting a significant portion of the gene. This gene is then inserted by ligation into a vector designed for facilitating chromosomal gene replacement. The *E. coli* cells are then transformed with those vectors. Cells that have incorporated the plasmid into the chromosome at the site of the target gene are selected, then the plasmid is forced to leave the chromosome by growing the cells on sucrose. Sucrose is toxic when the sacB gene resides in the chromosome. The properly mutated strain is selected based on its phenotype of tetracycline sensitivity and sucrose resistance. PCR analysis or DNA sequencing then confirms the desired genetic change.

The enzyme can be removed from the cell extract after cell disruption and before use. Any of the several means known in the art of protein purification may be used, including affinity purification techniques such as the use of antibodies or antibody fragments with specific affinity for the target enzymes; use of affinity tags expressed as part of the target enzymes to facilitate their removal from the cell extract; and conventional purification methods.

For example, an antibody or antibody fragment (e.g., Fab or scFv) is selected for specific affinity for the target enzyme using phage display or other well developed techniques. That antibody or antibody fragment is then immobilized on any of several purification beads or resins or membranes using any of several immobilization techniques. The immobilized antibody is contacted with the cell extract to bind to the target enzyme, and the immobilized antibody/enzyme complex then removed by filtration or gentle centrifugation.

In another example, the coding sequence of the targeted protein may be modified to include a tag, such as the Flag® extension (developed by Immunex Corp. and sold by Stratagene), or a poly-histidine tail. Many other examples have been published and are known to those skilled in the art. The tagged proteins are then removed by passage over the appropriate affinity matrix or column. The amino acid extension and binding partner are chosen so that only specific binding occurs under conditions compatible with the stability of the cell extract, and without significantly altering the chemical composition of the cell extract.

In yet another example, the target enzyme or enzymes are separated by any of several methods commonly used for protein purification, such as substrate affinity chromatography, ion exchange chromatography, hydrophobic interaction chromatography, electrophoretic separation, or other methods practiced in the art of protein purification.

Redox optimized extracts. The biological extracts for the present methods are optimized to substantially eliminate enzymes and other biomolecules present in the extract that act to reduce the redox buffer. Certain undesirable enzymes, e.g. glutathione reductase, are genetically inactivated or removed from the cell extracts utilized in the reaction mixture. Additionally, the reaction mixture may be treated with low concentrations of an inactivating agent as described above. The optimal concentration of such treatment, if any, can be readily determined by methods such as those illustrated in the example experiments described.

Redox buffer. The synthetic reaction mix in the present invention may be modified by the addition of a redox buffer. Such a buffer comprises compounds with free sulfhydryl groups and/or disulfide bonds, such as one or more of glutathione, cysteine, homocysteine etc. in either their reduced or oxidized forms or in a mixture of both. The concentration of reducing and/or oxidizing agent and the ratio of the oxidized and reduced forms necessary to achieve the reducing or oxidizing power desired for the selected reaction time will vary according to the strength of the reducing or oxidizing agent, the level of $O_2$ in the system, and the length of the reaction time.

In a preferred embodiment, glutathione is used as the redox buffering agent, and is added at a concentration of at least about 1 mM and not more than about 25 mM, preferably at a concentration of about 2 to 10 mM.

The redox buffer may comprise both the oxidized and reduced forms of the sulfhydryl compound, for example in a ratio of between about 10:1 to 1:5 of oxidized:reduced forms, usually in a ratio between about 5:1 to 2:1, and may be in a ratio of 4:1.

Addition of folding enzymes. The reaction mixture of the present invention may be further modified by the inclusion of one or more enzymes that enhance folding and disulfide bond formation, i.e. foldases, chaperonins, etc. In one embodiment of the invention, a bacterial foldase enzyme is added to the reaction mix. A number of cysteine oxidoreductases catalyzing disulfide bond formation have been characterized in *E. coli*, for example. Enzymes or chaperonins of interest include RotA (PpiA), FkpA, Skp, SurA, PpiD, DsbA, DsbB, DsbC, DsbD, PDI (protein disulfide isomerase), GroEL/ES, DnaK, DnaJ, GrpE, BIP (immunoglobulin heavy chain binding protein), PPI (peptidylprolyl isomerase) and cyclophilins, etc. (see Schafer et al. (1999) J Biol Chem 274(35):24567-74; Muller et al. (2001) Prog Nucleic Acid Res Mol Biol. 66:107-57). The folding enzyme(s) are added at a concentration effective to improve the overall activity of the target protein of interest, which may be empirically determined by titrating the biological activity of the expressed protein product.

Of particular interest is the inclusion of DsbC, a soluble enzyme with oxidase and isomerase activity that catalyzes the rearrangement, or isomerization, of incorrect disulfide bonds. Incorrect pairing of cysteine residues occurs readily when an unfolded polypeptide chain is first oxidized. DsbC facilitates the disruption of incorrect disulfide bonds and the subsequent formation of those that occur in the native state. Also of interest is the use of the soluble enzyme DsbA, which is a main catalyst of disulfide bond formation.

Identification of the DsbC gene is described by Missiakas et al. (1994) EMBO J 13:2013-2020, where it is shown to have an activity similar to that of DsbA in the dithiothreitol-dependent reduction of insulin in vitro. Also see Chen et al. (1999) J. Biol. Chem. 274:19601-19605. The use of DsbA or DsbC for enhancing periplasmic folding is discussed by Joly et al. (1998) P.N.A.S. 95:2773-2777.

Bacterial periplasmic chaperone proteins belong to two major groups, the Dsb proteins catalyzing thiol-disulfide exchange reactions, and peptidyl prolyl isomerases (PPlases) catalyzing the cis-trans isomerization around Xaa-Pro peptidyl bonds. Representatives of all major families of PPlases have been detected in the periplasm of Gram-negative bacteria, including RotA (PpiA), which is a cyclophilin-type PPlase; FkpA, a FK506-binding protein type PPlase; and SurA and PpiD, which belong to the parvulin type. In addition, Skp functions as a periplasmic chaperone. This 16-kDa, basic *E. coli* protein is a homolog of the Salmonella OmpH protein, which acts a molecular chaperone preventing premature folding of preproteins, and in the generation and maintenance of early soluble folding intermediates.

As an alternative to bacterial enzymes, eukaryotic enzymes may be used. For example, the eukaryotic PDI is not only an efficient catalyst of protein cysteine oxidation and disulfide bond isomerization, but also exhibits chaperone activity. Co-expression of PDI can even facilitate the production of active proteins having multiple disulfide bonds.

The terms "desired protein" or "selected protein" are used interchangeably and refer generally to any peptide or protein having more than about 5 amino acids. The polypeptides may be homologous to, or preferably, may be exogenous, meaning that they are heterologous, i.e., foreign, to the bacteria from which the bacterial cell-free extract is derived, such as a human protein or a yeast protein produced in the bacterial cell-free extract. Preferably, mammalian polypeptides, i.e. polypeptides encoded in a mammalian genome are used.

Examples of mammalian polypeptides include, but are not limited to, molecules such as renin; growth hormones, including human growth hormone and bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

Methods and Systems for Cell-Free Protein Synthesis

As noted above, the subject invention is drawn to methods and systems for the synthesis of biologically active proteins, particularly proteins comprising one or more disulfide bonds. The reaction mix for cell-free protein synthesis is modified to improve protein folding and formation of disulfide bonds, which methods may include the use of energy sources lacking high-energy phosphate bonds, e.g. glucose and glycolytic intermediates.

In cell-free protein synthesis systems directed to producing proteins with one or more disulfide bonds, a redox buffer may be included in the reaction mix to maintain the appropriate oxidizing environment (for example by the inclusion of glutathione in an appropriate ratio of oxidized to reduced forms). The redox buffer is stabilized by inactivating oxidoreductase reactions driven by endogenous proteins in the bacterial extract employed in the system.

In the methods of the invention, the in vitro synthesis system contains a cellular extract derived from a bacterial strain in which the glutathione reductase gene (gor) has been inactivated (e.g., mutated or deleted). The extract may be treated with a low concentration of a compound that inactivates free sulfhydryl groups. In embodiments employing IAM, the concentration of IAM in the synthesis reaction is from about 5 µM to about 500 µM, such as from about 10 µM to about 100 µM, and including from about 20 µM to about 75 µM. In certain embodiments, the concentration of IAM in the in vitro protein synthesis reaction is 50 µM. By reducing the amount of compounds that inactivate free sulfhydryl groups required to produce disulfide-bond containing proteins, the present invention allows non-high energy phosphate bond-containing energy sources to be used.

In certain embodiments, the bacterial strain from which the cellular extract is derived is further genetically modified such that the protein produced from the thioredoxin reductase gene includes an affinity tag (e.g., a hemagglutinin tag, HA). In certain of these embodiments, prior to synthesis, a cellular extract from this bacterial strain is contacted to an affinity resin which selectively binds to the affinity tag on the modified thioredoxin reductase protein and removes it from the extract. This further prevents reduction of the redox buffer used in the production of proteins that include disulfide bonds.

The in vitro synthesis may be further enhanced by the inclusion of accessory proteins that assist in the proper folding of proteins in vivo. Of particular interest is the inclusion of foldases, proteins with a catalytic activity that serve to accelerate rate-limiting steps in folding, e.g. RotA (PpiA), FkpA, Skp, SurA, PpiD, DsbA, DsbB, DsbC, DsbD, PDI, GroEL/ES, DnaK, DnaJ, GrpE, BIP, PPI, PDI, cyclophilin, etc.

For some synthetic reactions, e.g. multiplexed reactions, it is preferable to use batch rather than a semi-continuous system. For batch synthesis methods, the reaction mix is preferably modified to decrease the activity of molecules in the extract, e.g. endogenous enzymes, that have reducing activity.

In one embodiment of the invention, methods are provided for screening in vitro synthesis reaction conditions in order to optimize folding and correct formation of disulfide bonds. A plurality of reactions having a stable redox potential are assayed for synthesis of the active form of a protein containing at least one disulfide bond, i.e. a protein that is correctly folded.

The reaction conditions are optimized by varying the level of compounds that irreversibly inactivate free sulfhydryl groups, and by introducing selected chaperone and foldase protein(s); varying temperature; varying the concentration of the redox buffer as well as the ratio of oxidized to reduced forms; and the like.

A typical assay contains a control sample, which may be a conventional reaction mixture, and/or a redox stabilized reaction mixture. The reaction conditions may be optimized by adding or varying the concentrations of one or more of RotA (PpiA), FkpA, Skp, SurA, PpiD, DsbA, DsbB, DsbC, DsbD, PDI, GroEL/ES, DnaK, DnaJ, GrpE, BIP, PPI, PDI, cyclophilin, etc. to at least one and usually a plurality of reactions to form a panel of reaction conditions. The change in synthesis of active protein in response to the agent is measured. Reaction conditions may also be optimized by varying the temperature, varying the concentration of inactivating agent, and varying the ratio of oxidized to reduced forms of the redox buffer to form a plurality of reaction conditions, which may be displayed as a matrix of possible combinations.

A plurality of assays may be run in parallel with different agent concentrations to obtain a differential response to the various concentrations. As known in the art, determining the effective concentration of an agent typically uses a range of concentrations resulting from 1:10. or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in synthesis.

The amount of protein produced in a translation reaction can be measured in various fashions. One method relies on the availability of an assay, which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^3$H-leucine, or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

In addition to the components described above, in vitro protein synthesis protein reactions of the invention include certain other components, some of which are described below.

For example, the reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001. herein incorporated by reference.

In one embodiment of the invention, the reaction chemistry is as described in co-pending patent application U.S. Ser. No. 10/643,683, filed Aug. 18, 2003, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a system homeostatic in [PO$_4$] and pH, in which synthesis can occur even in the absence of secondary energy sources.

The template for cell-free protein synthesis can be either mRNA or DNA. Translation of stabilized mRNA or combined transcription and translation converts stored information into protein. The combined system, generally utilized in E. coli systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally between pH 6 and pH 9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome of the extract source cells.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars. In embodiments where polynucleotide synthesis occurs, the reaction mix will include nucleotide tri-phosphates (NTPs). While these monomers have high-energy phosphate bonds, they are not employed as energy sources for the protein synthesis reaction.

The reactions may be large scale, small scale, or may be multiplexed to perform a plurality of simultaneous syntheses. Additional reagents may be introduced to prolong the period of time for active synthesis. Synthesized product is usually accumulated in the reactor and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include E. coli extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, putrescine, spermine, spermidine, etc.

The salts preferably include potassium, magnesium, and ammonium salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine or optionally, in combination, putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Materials and Methods
Construction of the KGK10 Strain. The objective here was to delete the gene encoding glutathione reductase (Gor) and to add the coding sequence for a hemagglutinin tag (HA Tag) to the trxB gene. For the latter, a PCR cassette was generated using the primers TrxB-HAFor (5'-tgatgcggaacgctacctcgatg-gtttagctgacgcaaaatacccatat-gacgtcccggactacgcctaataaGTGTAG GCTGGAGCT-GCTTC) and TrxB-HARev (5'-gtcgcatggtgtcgccttctttactttgttactgatttCA TATGAATATCCTCCTTAGT) with the pKD3 plasmid template as described (Datsenko and Wanner (2000) Proc Natl Acad Sci USA 97:6640-5). In these primers, regions of homology are shown in lower case, the HA tag sequence is underlined, stop codons are in bold, and regions that anneal to the pKD3 plasmid are in capital letters. The cassette was transformed into the BW25113 pDK46 strain and selected on LB-Chloramphenicol. P1 bacteriophage transduction was used to move the genomic modification from a successful recombinant into KC6. FLP recombinase expression from the pCP20 plasmid was then used to remove the chloramphenicol resistance marker resulting in the strain KC6 TrxB-HA.

Glutathione reductase (gor) was deleted from KC6 TrxB-HA using the same procedure as above. The PCR cassette was generated with the primers Gor-DelFor (5'-ggagtaattgcagc-cattgctggcacctattacgtctcgcGT-GTAGGCTGGAGCTGCTTC) and Gor-DelRev (5'-aacg-taattaagggctaagagcacactactcttagcccttCATATGAATATCCTCCTTAGT). The trxB, gor, and ahpC loci of KGK10 were sequenced to verify that gor was deleted, trxB had acquired a 3' HA tag sequence, and ahpC had not mutated.

Extract Preparation and Affinity Purification of TR from KGK10. KGK10 or KC6 were grown in a 10-liter fermentor using a defined medium with glucose and amino acids fed to the fermentor using a procedure that allows logarithmic growth to high cell density while avoiding the accumulation of acetate (Zawada and Swartz (2005) Biotechn and Bioeng 89:407-415). The fermentation was harvested at 30 $OD_{600}$ and extract was prepared as described by Liu et al. (2005) Biotech Prog 21:460-465.

To remove the HA tagged thioredoxin reductase from the KGK10 extract, an AP-Mini (Waters, Milford Mass.) 5 mm inner diameter chromatography column was packed with 1.8 mL of anti-HA resin (Roche Applied Science, Indianapolis, Ind., catalog # 1 867 423). The column was conditioned with 50 mL of equilibration buffer (20 mM Tris, 0.1 M NaCl, 0.1 mM EDTA, pH 7.5). A total of 15 mL of KGK10 extract was then passed over the column at a flow rate of 0.25 mL/min. One half milliliter fractions of flow-through were collected. The column was then washed with 10 mL of equilibration buffer+0.05% Tween-20. Bound TrxB was eluted with 0.1 M glycine pH 2.0.

Cell-free Protein Synthesis Reactions. All chemicals were purchased from Sigma-Aldrich (St. Louis, Mo.) except where indicated. Two similar cell-free protein synthesis systems were used in this work. Both systems included the following standard components: 130 mM potassium glutamate; 10 mM ammonium glutamate; 1.2 mM AMP; 0.85 mM each of GMP, UMP, and CMP; 1.5 mM spermidine; 1.0 mM putrescine; 34 μg/mL folinic acid; 170.6 μg/mL E. coli tRNA mixture (Roche, Indianapolis Ind.); 10 mM potassium phosphate (pH 7.2); 20 natural amino acids at 2 mM each; 5 μM L-[U-$^{14}$C]-Leucine (Amersham Pharmacia, Uppsala Sweden); 0.33 mM nicotinamide adenine dinucleotide (NAD); 0.27 mM coenzyme A (CoA); 26.6 μg/mL plasmid; 100 μg/mL T7 RNA polymerase; and 0.24 volumes E. coli S30 extract. The PANOx-SP system also included 16 mM magnesium glutamate; 33 mM phosphoenol pyruvate (PEP; Roche, Indianapolis Ind.); and 2.7 mM sodium oxalate. In addition to the standard reagents, the glucose system contained 8 mM magnesium glutamate; 90 mM Bis-Tris buffer pH 7.0; and 33 mM glucose.

Combined transcription-translation reactions were carried out in 1.5 mL Eppendorf tubes at 37° C. for 3 hours unless otherwise noted. The plasmids were prepared using a Qiagen Plasmid Maxi Kit (Qiagen, Valencia Calif.). T7 RNA polymerase was prepared from *E. coli* strain BL21 (pAR1219) as described previously (Davanloo et al. (1984) Proc Natl Acad Sci 81:2035-9). DsbC was prepared by overexpression and purification from the strain BL21 (DE3) (pETDsbChisC) as described (Yin and Swartz (2004) Biotechnol Bioeng 86:188-95). In reactions requiring iodoacetamide (IAM) treatment of the extract, a small volume of concentrated IAM was first added to the bottom of an Eppendorf tube. A much larger volume of S30 extract was then rapidly and thoroughly mixed with the small volume of IAM. The extract was incubated with the IAM for 30 minutes at room temperature before being used in the in vitro synthesis reaction.

For determining the effect of pH and IAM concentration on GSSG stabilization, the pH of S30 extracts was adjusted by first adding a small volume of 10 M KOH or HCl to the bottom of an Eppendorf tube. A much larger volume of S30 extract was then rapidly mixed with the small volume of acid or base. The pH was measured with a standardized micro-pH probe (Model 9810BN, Orion, Beverly, Mass.). Several 15 µL PANOx-SP reactions supplemented with 5 mM GSSG and the pK7CAT plasmid were prepared at each pH and IAM concentration. Single reactions were terminated at 15, 38, 60, 90, 120, and 180 minutes for each condition, and the concentration of SH groups was measured as described below.

Urokinase (UK) reactions were 30 µL total volume PANOx-SP reactions supplemented with the pK7UK plasmid, 4 mM GSSG, 1 mM GSH, and 75 µg/mL DsbC. The reactions were incubated for 6 hours at 37° C. The plasmid pK7UK encodes for the serine protease domain of murine urokinase under control of the T7 promoter.

Murine granulocyte macrophage-colony stimulating factor (mGM-CSF) reactions were 30 µL total volume PANOx-SP reactions supplemented with the pK7catgmhis plasmid, 4 mM GSSG, 1 mM GSH, and 100 µg/mL DsbC. The gene for mGM-CSF was fused with the codons for the first five amino acids of chloramphenicol acetyl transferase (CAT) to improve translation initiation and the codons for a hexahistidine purification tag were added just before the stop codon. This modified gene was cloned into the pK7 plasmid to create pK7catgmhis (Yang et al. (2004) Biotechnol Prog 20:1689-95). The modified 5' coding sequence has been shown to increase translation rate and not significantly affect protein folding.

Glucose system reactions were conducted in the same manner as the 15 µL and 30 µL total volume PANOx-SP reactions and used the pK7CAT or pK7catgmhis plasmid. The reactions were incubated for 3 (CAT) and 5 (mGM-CSF) hours at 37° C. The plasmids encode for each respective gene between the T7 promoter and the T7 terminator.

Measurement of Protein Synthesis Yield. A five-microliter sample of the in vitro synthesis reaction was spotted onto a piece of filter paper immediately after the reaction. The amount of L-[U-$^{14}$C]-Leucine incorporated into the protein was measured using the trichloroacetic acid procedure described previously to precipitate the synthesized protein (Calhoun and Swartz (2005) Biotechnol Prog 21:1146-53) which was quantified with a liquid scintillation counter (LS3801, Beckman Coulter, Inc.). The soluble fraction of the product protein was isolated by centrifuging the sample at 14,000×g for 15 min and 4° C. Five microliters of the supernatant were used to measure the incorporation of L-[U-$^{14}$C]-Leucine in the same way.

Assay for the Reduction of Oxidized Glutathione. The reduction of oxidized glutathione was measured by monitoring the increase in concentration of sulfhydryl groups over time. The entire 15 µL in vitro synthesis reaction was diluted with an equal volume of 10% trichloroacetic acid and centrifuged for 10 minutes at 12,000×g and 4° C. Ten microliters of the supernatant was added to wells of a 96-well microtiter plate. To each well, 90 µL of 1 M Tris-HCl (pH 7.8) with 0.44 mg/mL DTNB (5,5'-dithiobis-2-nitrobenzoic acid, TCI America) was added. After 3 minutes at room temperature, the absorbance at 412 nm was measured and the concentration of free thiols determined by comparison to a standard curve determined with GSH solutions of known concentration.

Assay for Thioredoxin Reductase Activity. Thioredoxin reductase was produced in in vitro synthesis reactions as described previously (Knapp and Swartz (2004) FEBS Lett 559:66-70). The pHs of aliquots of the unpurified reaction product were adjusted to the desired values with small volumes of concentrated KOH or HCl. These aliquots were then mixed with a small volume of IAM concentrate to obtain a final IAM concentration of 7 mM. These samples were incubated at room temperature for 30 minutes, and then the thioredoxin reductase activity of the samples was measured. The activity assay for thioredoxin reductase contained the following components: 50 mM NaH$_2$PO$_4$ pH 7.6, 1.5 mM EDTA, 10 mM glucose 6-phosphate, 200 µM DTNB, 300 µM NADPH, 3 µM *E. coli* thioredoxin (EMD Biosciences; Darmstadt, Germany), and 0.2 U glucose 6-phosphate dehydrogenase (Sigma). Approximately 500 ng of thioredoxin reductase was added to 1 mL of the assay mixture and the rate of increase in absorbance at 412 nm was measured for 90 seconds at 37° C. DTNB produces two molecules of nitrothiobenzoate when it is reduced. The extinction coefficient of nitrothiobenzoate (13,600 M$^{-1}$ cm$^{-1}$) was used to calculate the rate of reaction.

Assay for the Activity of Cell-Free Synthesized Urokinase. After centrifugation, 10 µL of supernatant was added to a microtiter plate well containing 80 µL of assay buffer (50 mM Tris-HCl, 38 mM NaCl pH 8.8) and 10 µL of substrate solution (2 mM Chromozym U; Roche Applied Science). The rate of change of absorbance at 405 nm was measured in a microplate reader (SpectraMax 190, Molecular Devices). The serine protease domain of murine urokinase was produced, purified, and assayed as described (Kim and Swartz (2004) Biotechnol Bioeng 85:122-9). That work indicated that 87 ng of enzyme produces an activity of 10 mOD-mL/min. The yield of active UK was calculated based on that specific activity.

Assay for the Cell Proliferation Activity of Cell-Free Synthesized Murine GM-CSF. The biological activity of mGM-CSF was assayed by its ability to induce the proliferation of a murine GM-CSF-dependent cell line, NFS-60. The NFS-60 cells were grown on RPMI media (Invitrogen) with 10% FCS in the presence of yeast-derived GM-CSF (Immunex). Cells were harvested in log phase, washed three times, and plated at a concentration of 5000 cells per well in a standard 96-well tissue culture plate. Triplicate dilutions of standard *E. coli* derived mGM-CSF (R&D Systems, Minneapolis, Minn.) or cell-free expressed mGM-CSF were added to the wells and incubated in a 5% CO$_2$ environment at 37° C. After approximately 20 h, 6.7 µCi/mL [$^3$H]-thymidine (Amersham Biosciences) was added and incubation was resumed. The cells were harvested onto glass fiber filter mats 7 to 10 hours later, and [$^3$H]-thymidine incorporation was measured with a Wallach 1450 Micro-beta scintillation counter (PerkinElmer, Wellesley, Mass.).

Results

We made two chromosomal changes to the strain KC6 (Calhoun and Swartz (2006) J Biotechnol. 123:193-203) that when combined with an affinity removal step resulted in a cell-free extract devoid of all known cytoplasmic reduction pathways. The first mutation was to delete gor, eliminating the enzyme that catalyzes the reduction of GSSG. The data shown in FIG. 1A indicate that this deletion does not completely stabilize GSSG (KGK10 cell extract). We reasoned that the continued reduction of GSSG in Δgor strains was due to the activity of the thioredoxin reductase (TrxB) mediated system.

The gene for thioredoxin reductase (trxB) cannot be deleted in the Δgor background without a compensatory mutation in ahpC that restores the ability of the cytoplasm to reduce disulfide bonds. In order to disable the thioredoxin system, a hemagglutinin purification tag (HA Tag) was added to the C-terminus of trxB in the chromosome. The final strain was named KGK10 (A19 ΔspeA ΔtnaA ΔtonA ΔendA ΔsdaA ΔsdaB ΔgshA Δgor TrxB-HA met+). This strain grows normally without acquiring the AhpC mutation because the thioredoxin mediated reduction pathway is still intact. Yet, the purification tag allows TrxB to be removed from the extract before being used in in vitro synthesis reactions. TrxB-HA removal was verified by doping radioactive TrxB-HA into KC6 extract, and then removing it with the affinity chromatography procedure. More than 90% of the radioactive TrxB-HA was removed from the extract, and it was the only protein retained on the column.

Figure 1:
FIGS. 1A and 1B show the stabilization of GSSG in cell-free extracts with IAM derivatization at various pHs. The numbers are the rate of increase of free sulfhydryl groups over time ($\mu$M/min) in PANOx-SP reactions using the given extract inactivated at the indicated pH and IAM concentration. The degree of shading indicates the rate of reduction; dark gray for greater than 100 $\mu$M/min, light gray for 10-30 $\mu$M/min, and no shading for 10 to −10 $\mu$M/min. The standard deviation for the rate measurements is approximately 9% of the indicated value.

KGK10 cell extract was prepared and the HA tagged TrxB was removed using affinity chromatography. The KC6, KGK10, and KGK10-TrxB extracts were treated with various concentrations of IAM and then used in in vitro synthesis reactions containing 5 mM GSSG. FIG. 1A shows that the deletion of gor, but not the affinity purification of TrxB, significantly decreases the rate of reduction of GSSG. Twenty-fold less IAM was needed to stabilize the oxidized glutathione buffer in KGK10 extract versus KC6 extract.

The chromosomal changes in KGK10 reduced the required concentration of IAM, but did not eliminate the need for IAM pretreatment in order to stabilize GSSG. We reasoned that the concentration of IAM might be further reduced by carefully considering the chemistry of the reaction. A sulfhydryl group must be in the thiolate anion form to perform a nucleophilic attack on IAM. The vast majority of cysteinyl sulfhydryl groups in proteins have a pKa>8.0, and therefore remain protonated at physiological pH. However, the sulfhydryl groups of the cysteine residues in the active sites of redox-active proteins are more likely to be thiolate anions at neutral pH. These proteins lower the pKa of the active site thiols by charge interactions with neighboring amino acid residues. Performing the IAM treatment at a lower pH where most other sulfhydryl groups are protonated may preferentially protect cysteine residues that are not part of such an active site.

Figure 2:
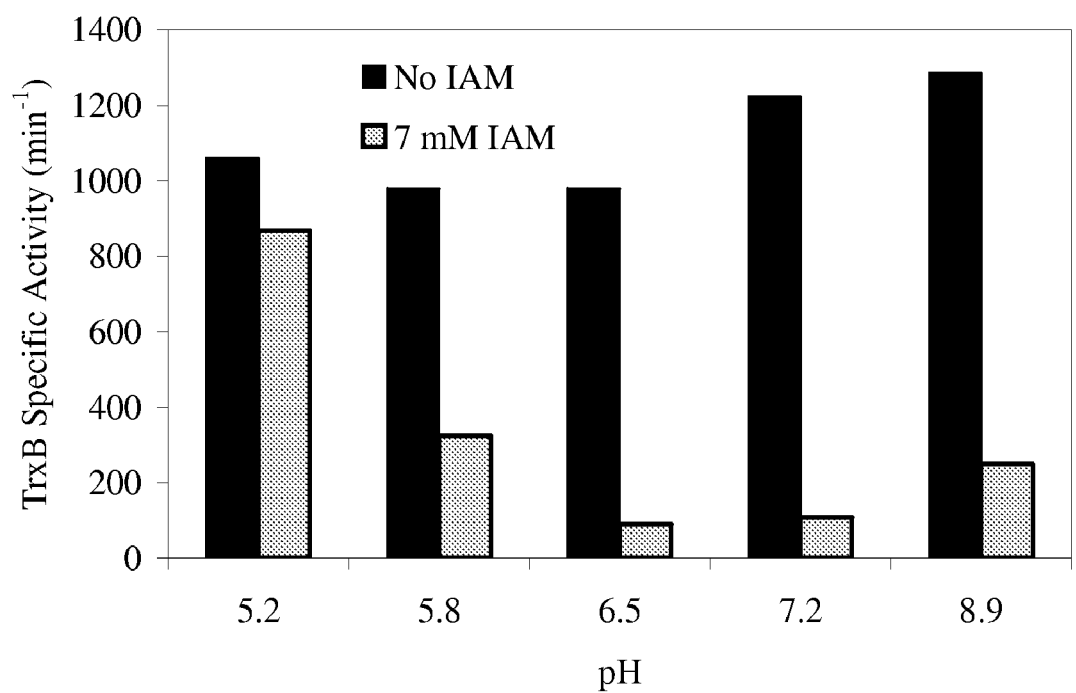
FIG. 2 is a bar graph depicting IAM inactivation of TrxB at various pHs. The enzyme's activity is not greatly affected by pH without IAM (black bars), but is greatly affected after treatment with IAM (gray bars).

In order to confirm the feasibility of this strategy, thioredoxin reductase was inactivated with IAM at various pHs. The pKa of the active site sulfhydryl of TrxB is 6.98. It appears from FIG. 2 that IAM inactivation of TrxB begins to lose its effectiveness around pH 5.8. approximately one unit below the pKa. This experiment verifies the theory that IAM inactivation will not occur below a certain pH (relative to the pKa of the cysteine in question), and suggests that the concentration of IAM required to stabilize GSSG in in vitro synthesis reactions might be reduced by preferentially inactivating reductases at low pH.

In practice, however, pretreating at lower pHs did not decrease the required concentration of IAM, as seen in FIG. 1B. KGK10 extracts treated with 10 μM or less IAM catalyze an increase in free sulfhydryl groups at between 20 and 30 μM/min regardless of treatment pH. Near physiological pH, 50 μM IAM is sufficient to eliminate the reduction of GSSG. Concentrations greater than 50 μM IAM lead to a slow rate of oxidation of sulfhydryls, similar to what is observed in reactions with no extract. As the pH of the IAM treatment is adjusted farther from physiological pH, greater concentrations of IAM are needed to fully stabilize the oxidized glutathione.

The primary objective of this work is not necessarily to totally stabilize GSSG, but to produce proteins that require disulfide bonds. In this pursuit, murine granulocyte macrophage-colony stimulating factor (mGM-CSF) was used as a model protein in cell-free reactions. It contains two disulfide bonds. FIG. 3 indicates that the oxidized glutathione buffer did not need to be completely stabilized to produce this protein. Nevertheless, the yield of active protein was 25 to 30% greater when KGK10 extract with either 50 μM IAM treatment or TrxB removal was used rather than IAM-treated KC6 extract.

The serine protease domain of murine urokinase (UK) requires six disulfide bonds, has been produced in in vitro synthesis, and is known to be highly dependant on disulfide isomerization (Kim and Swartz, Biotechnol Bioeng 85:122-9). The total, soluble, and active protein yields are presented in FIG. 4 for KC6, KGK10 extracts pretreated with different concentrations of IAM, and for the KGK10-TrxB extract. The established KC6 extract with 1 mM IAM pretreatment produced 43 μg/mL active protein. KGK10 extracts with 0, 10, 50, and 100 μM IAM pretreatment at pH 6.6 produced increasing amounts of active urokinase reaching a maximum of 53 μg/mL at 50 μM IAM. Anti-HA removal of TrxB from KGK10 extracts allowed nearly the same amount of active UK to be produced. Other cases were investigated including pretreatment of KGK10 at pH 5.5 with 600 μM IAM, but none had yields as high as those presented in FIG. 4.

To determine if the decreased concentration of IAM required for the KGK10 extract would preserve other sulfhydryl requiring activities such as glyceraldehyde 3-phosphate dehydrogenase, (which is required for glucose utilization), CAT and mGM-CSF production reactions were conducted. FIG. 5 shows that the 50 μM IAM pretreatment allows glucose to be used as an energy source when producing proteins that require disulfide bonds. In contrast to KC6, KGK10 reactions show a much smaller decrease in protein yield after IAM pretreatment.

This newly engineered cell-extract provides for more economically attractive production of proteins that require disulfide bonds. As shown in FIG. 5B, KGK10 reactions produce over 3-fold more active mGM-CSF than KC6 reactions when IAM and glucose are used. The amount of active mGM-CSF produced in a glucose reaction (FIG. 5B) is only 50% of that produced in a PEP reaction (FIG. 3) at optimal conditions. However, this is still economically attractive because PEP is the most expensive cell-free reaction component and is at least 1000 fold more expensive than glucose. The elimination of PEP paves the way for further cost reduction and commercialization of in vitro synthesis. In addition, this invention provides methods likely to preserve other activities in the cell extract useful for the production and folding of proteins and macromolecular assemblies.

What is claimed is:

1. A method for cell-free synthesis of properly folded polypeptides comprising at least one disulfide bond, the improvement comprising:
synthesizing said polypeptide in a reaction mix comprising a biological extract derived from a bacterial cell that has been genetically modified to inactivate glutathione reductase and pre-treated with low concentrations of a sulfhydryl inactivating agent;
wherein the low concentration of the sulfhydryl inactivating agent is equivalent in sulfhydryl inactivating activity to iodoacetamide at a concentration of from 10 μM to about 100 μM.

2. The method according to claim 1, wherein said sulfhydryl inactivating agent alkylates or acetylates free sulfhydryl groups.

3. The method of claim 2, wherein the sulfhydryl inactivating agent is iodoacetamide.

4. The method according to claim 1, wherein the biological extract is treated to remove thioredoxin reductase.

5. The method according to claim 4, wherein the bacterial cell from which the biological extract is derived is genetically modified such that said thioredoxin reductase protein comprises an affinity tag; and the treatment to remove the thioredoxin reductase comprises contacting the biological extract with an affinity resin specific for the affinity tag.

6. The method according to claim 1, wherein said reaction mix comprises an energy source lacking high energy phosphate bonds at a concentration of at least about 50 mM.

7. The method according to claim 6, wherein said energy source is glucose or a glycolytic intermediate lacking high energy phosphate bonds.

8. The method according to claim 1, wherein said reaction mix further comprises a redox buffer.

9. The method according to claim 8, wherein said redox buffer comprises one or more of glutathione, cysteine, and homocysteine.

10. The method according to claim 9, wherein said redox buffer comprises a mixture of oxidized and reduced glutathione.

11. The method according to claim 1, wherein said reaction mixture comprises one or more enzymes that enhance polypeptide folding or generation of disulfide bonds.

12. The method according to claim 11, wherein said one or more enzymes that enhance polypeptide folding or generation of disulfide bonds are foldase enzymes.

13. The method according to claim 1, wherein said reaction mixture is substantially free of polyethylene glycol.

14. The method according to claim 13, wherein said reaction mixture comprises one or more of spermine, spermidine and putrescine.

15. A reaction mix for cell-free protein translation, comprising a biological extract derived from a bacterial cell that has been genetically modified to inactivate glutathione reductase and pre-treated with low concentrations of a sulfhydryl inactivating agent;
wherein the low concentration of the sulfhydryl inactivating agent is equivalent in sulfhydryl inactivating activity to iodoacetamide at a concentration of from 10 μM to about 100 μM.

16. The reaction mix according to claim 15, wherein said sulfhydryl inactivating agent alkylates or acetylates free sulfhydryl groups.

17. The method of claim 16, wherein the sulfhydryl inactivating agent is iodoacetamide.

18. The reaction mix according to claim 15, wherein said biological extract is treated to remove thioredoxin reductase.

19. The reaction mix according to claim 18, wherein the bacterial cell from which the biological extract is derived is genetically modified such that said thioredoxin reductase protein comprises an affinity tag; and the treatment to remove the thioredoxin reductase comprises contacting the biological extract with an affinity resin specific for the affinity tag.

20. The reaction mix according to claim 15, wherein said reaction mix comprises an energy source lacking high energy phosphate bonds, at a concentration of at least about 50 mM.

21. The reaction mix according to claim 20, wherein said energy source is glucose or a glycolytic intermediate lacking high energy phosphate bonds.

* * * * *

UNITED STATES PATENT AND TRADEMARK OFFICE
CERTIFICATE OF CORRECTION

| | | |
|---|---|---|
| PATENT NO. | : 7,871,794 B2 | Page 1 of 1 |
| APPLICATION NO. | : 12/016763 | |
| DATED | : January 18, 2011 | |
| INVENTOR(S) | : Kurtis G. Knapp et al. | |

It is certified that error appears in the above-identified patent and that said Letters Patent is hereby corrected as shown below:

On the Title Page

• Item (75) Inventors: Please replace "Swarts" with --Swartz--.

Signed and Sealed this
Thirty-first Day of January, 2012

David J. Kappos
*Director of the United States Patent and Trademark Office*